(12) United States Patent
Trexler

(10) Patent No.: US 12,109,101 B2
(45) Date of Patent: Oct. 8, 2024

(54) PROSTHETIC DEVICE ADHESIVE SYSTEM

(71) Applicant: C.R. Bard, Inc., Murray Hill, NJ (US)

(72) Inventor: Jonathan Bruce Trexler, Rehoboth, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 927 days.

(21) Appl. No.: 16/976,659

(22) PCT Filed: Mar. 1, 2019

(86) PCT No.: PCT/US2019/020191
§ 371 (c)(1),
(2) Date: Aug. 28, 2020

(87) PCT Pub. No.: WO2019/169213
PCT Pub. Date: Sep. 6, 2019

(65) Prior Publication Data
US 2020/0405468 A1 Dec. 31, 2020

Related U.S. Application Data

(60) Provisional application No. 62/637,360, filed on Mar. 1, 2018.

(51) Int. Cl.
*A61F 2/00* (2006.01)

(52) U.S. Cl.
CPC .... *A61F 2/0063* (2013.01); *A61F 2210/0085* (2013.01); *A61F 2220/0008* (2013.01);
(Continued)

(58) Field of Classification Search
CPC ............ A61F 2/0063; A61F 2002/0068; A61F 2002/0072; A61F 2002/7806;
(Continued)

(56) References Cited

U.S. PATENT DOCUMENTS 5,786,216 A 7/1998 Dionne et al.
6,736,854 B2 5/2004 Vadurro et al.
(Continued)

FOREIGN PATENT DOCUMENTS

WO WO-2017027461 A1 * 2/2017 ........... A61F 2/0063

OTHER PUBLICATIONS

International Search Report and Written Opinion for International Application No. PCT/US2019/020191, mailed May 23, 2019.
(Continued)

*Primary Examiner* — Katherine H Schwiker
*Assistant Examiner* — Zehra Jaffri
(74) *Attorney, Agent, or Firm* — Wolf, Greenfield & Sacks, P.C.

(57) ABSTRACT

An implantable prosthesis and a method of attaching the prosthesis to a tissue structure disclosed. The prosthesis includes a body having a first side arranged to face the tissue structure having a defect and second side opposite the first side. One or more adhesive-filled pods are disposed on the first side of the body and selectively openable to supply an adhesive in between the tissue structure and the first side of the prosthesis body after the prosthesis body is positioned relative to the defect. The pods may be pierced, punctured, broken, and/or ruptured to supply the adhesive. A deployment device having a piercer may be used to puncture the pods.

13 Claims, 9 Drawing Sheets

(52) U.S. Cl.
CPC . *A61F 2220/005* (2013.01); *A61F 2250/0071* (2013.01); *A61F 2250/0097* (2013.01)

(58) Field of Classification Search
CPC ...... A61F 2210/0085; A61F 2220/0008; A61F 2220/005; A61F 2250/0071; A61F 2250/0097; A61F 2013/53925; A61F 13/0246; A61F 13/0253
See application file for complete search history.

(56) References Cited

U.S. PATENT DOCUMENTS

| | | | | |
|---|---|---|---|---|
| 2004/0172048 | A1* | 9/2004 | Browning | A61F 2/0036 606/151 |
| 2008/0154228 | A1* | 6/2008 | Ortiz | A61B 17/1114 604/500 |
| 2010/0189764 | A1 | 7/2010 | Thomas et al. | |
| 2011/0189270 | A1* | 8/2011 | Broom | A61F 2/0063 424/451 |
| 2012/0065222 | A1 | 3/2012 | Fischell et al. | |
| 2012/0083651 | A1 | 4/2012 | Browning | |
| 2012/0175401 | A1* | 7/2012 | Bachman | A61B 17/0684 227/177.1 |
| 2013/0035415 | A1 | 2/2013 | Milbocker | |
| 2015/0073445 | A1* | 3/2015 | Griffin | A61L 27/56 606/151 |
| 2016/0106538 | A1 | 4/2016 | Mitra et al. | |
| 2016/0194425 | A1 | 7/2016 | Mitra et al. | |
| 2017/0333033 | A1* | 11/2017 | Valentine | A61B 17/068 |

OTHER PUBLICATIONS

International Preliminary Report on Patentability for International Application No. PCT/US2019/020191, mailed Sep. 10, 2020.

* cited by examiner

PROSTHETIC DEVICE ADHESIVE SYSTEM

CROSS-REFERENCE TO RELATED APPLICATIONS

This application is a National Stage filing under 35 U.S.C. § 371 of International Application No. PCT/US2019/020191, filed on Mar. 1, 2019, which claims priority under 35 U.S.C. § 119(e) to U.S. Provisional Application No. to U.S. 62/637,360, entitled "PROSTHETIC DEVICE ADHESIVE SYSTEM" and filed Mar. 1, 2018, the contents of each which are incorporated herein by reference in their entireties.

FIELD

The present invention relates to an implantable prosthesis and, more particularly, to systems for fixating the prosthesis to a tissue during soft tissue repair and reconstruction.

BACKGROUND

Various prosthetic devices have been proposed to repair and reinforce anatomical defects, such as tissue and muscle wall hernias. For example, ventral and inguinal hernias are commonly repaired using a sheet of biocompatible fabric, such as a knitted polypropylene mesh (BARD MESH). The fabric is typically sutured, stapled or otherwise provisionally anchored in place over, under or within the defect. Tissue integration with the fabric, such as by tissue ingrowth into and/or along the fabric, eventually completes the repair.

SUMMARY

According to one embodiment an implantable prosthesis for repairing a soft tissue defect is disclosed. The implantable prosthesis includes a prosthesis body having a first side arranged to face a tissue structure having a defect and second side opposite the first side, and one or more adhesive-filled pods disposed on the first side of the body, the one or more adhesive filled pods being selectively openable to supply an adhesive.

According to still another embodiment a method of repairing a soft tissue defect is disclosed. The method includes placing a prosthesis relative to a defect in a tissue structure, the prosthesis having a prosthesis body with a first side facing the tissue structure and a second side opposite the first side, and selectively releasing an adhesive from one or more pods disposed on the first side of the body after the prosthesis is placed relative to the defect.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF INVENTION

Figure 1A:
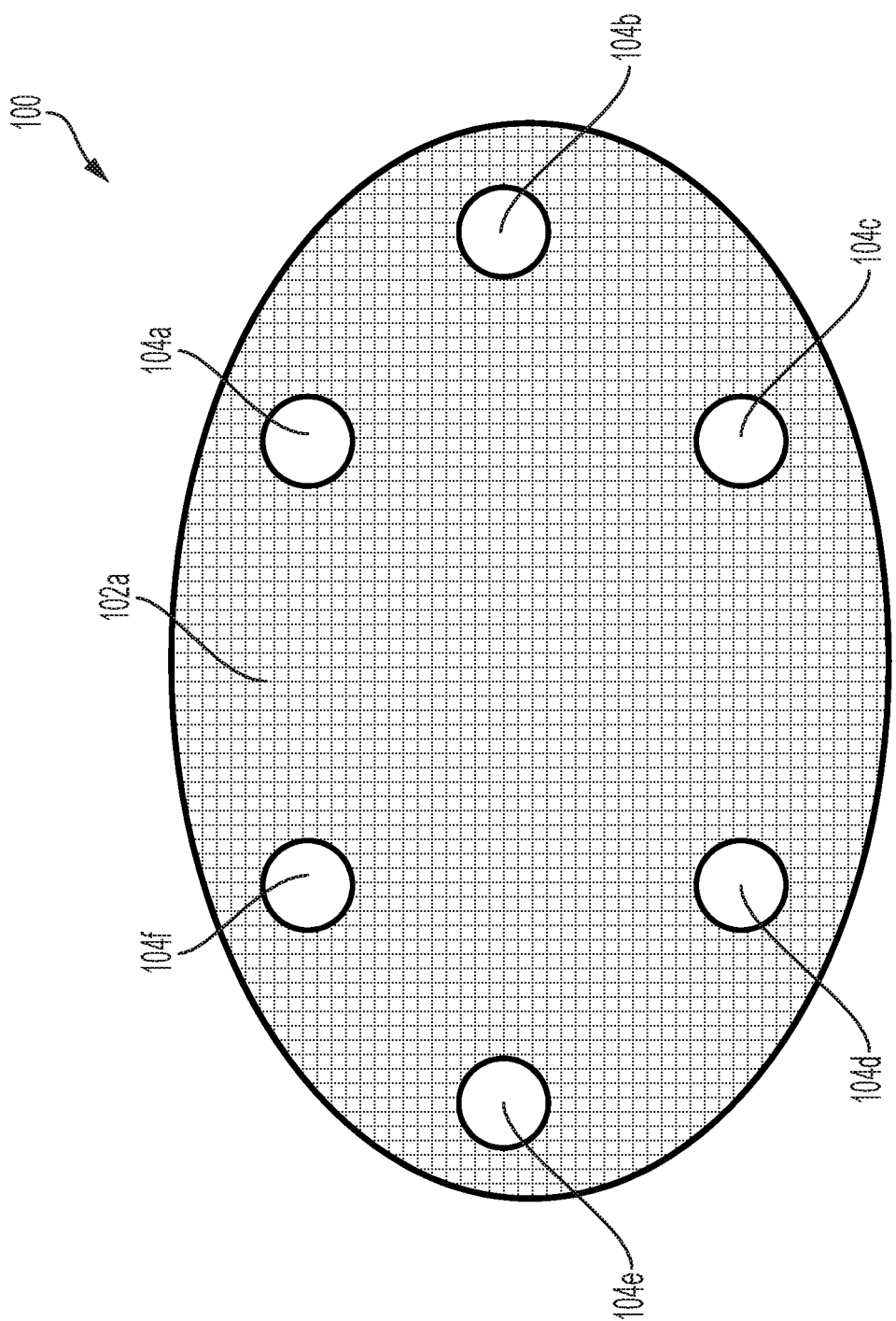
FIG. 1A is a schematic top view of an implantable prosthesis having a pod adhesive system according to embodiments of the present disclosure.

Implantable prostheses are used for repairing soft tissue defects, such as ventral and inguinal hernias, and/or in chest wall reconstruction, by promoting tissue integration with the implantable prosthetic, such as by tissue ingrowth. Typically, such prostheses are sutured, stapled or otherwise anchored in place over, under or within the defect. Tissue integration with the fabric, such as by tissue ingrowth into and/or along the fabric, eventually completes the repair.

During some procedures, an adhesive may be used to attach, or augment the attachment, of a prosthesis to a tissue layer. The inventors have recognized that in such procedures, if the adhesive is applied to a side of the mesh prior to placement of the mesh in the body cavity (e.g., over or under the defect), insertion and/or manipulation of the mesh may be difficult due to the exposed adhesive. For example, the mesh may become adhered to tissue other than the tissue at or near the defect. The adhesive layer also may become compromised during mesh placement if the adhesive is pre-applied, which could negatively impact the strength of fixation of the mesh to the tissue.

The inventors have also recognized that while the adhesive may be applied to the mesh using a separate applicator during a surgical procedure, deployment of the adhesive may be challenging and/or inconsistent. For example, deployment of the adhesive may need to be made laparoscopically underneath the mesh, between the mesh and the tissue. However, depending on the thickness of the mesh and/or the space between the mesh and the tissue, the deployment depth at which the adhesive is to be applied may vary. For example, with a thick mesh, the applicator tip may need to penetrate deeper to get past the mesh and avoid adhesive on the internal, cavity side, of the mesh. With thinner meshes, the applicator may need to penetrate less to avoid application of the adhesive deep inside the tissue, resulting in minimal surface contact with the mesh.

In view of the above, the inventors have realized that advantages may be achieved via an adhesive system in which one or more adhesive-filled pods are pre-placed on one side of the mesh. In such embodiments, the pods are selectively openable and arranged to supply the adhesive for attachment after placement of the mesh in the body cavity relative to the defect. For example, the pods may be ruptured, punctured, pierced, broken or otherwise opened to supply the adhesive between the tissue and the mesh after placement of the mesh. For purposes herein, pods may include capsules, pouches, or other suitable structures capable of encapsulating an adhesive material. In some embodiments, the pods are located on a side of the mesh that is facing and positionable against the tissue.

In some embodiments, the pods include an encapsulated, biocompatible adhesive arranged to fixate the mesh prosthesis to the tissue. In some embodiments, the adhesive includes a two-part adhesive that is mixed and activated upon breaking or other opening of the pods and releasing of the encapsulated materials, such as during the surgical procedure. In such embodiments, a first pod may include a base resin and the second capsule may include an activator or hardener. In other embodiments, the adhesive may include a pressure-sensitive adhesive material.

In some embodiments, fixation of the mesh to the tissue may take place during the surgical procedure. The fixation also may occur during another suitable time, such as during an initial healing process, e.g., during the first 6 to 8 weeks after the surgical procedure.

In some embodiments, the adhesive is encapsulated in a non-adhesive material. In some embodiments, the non-adhesive material is arranged to prevent unwanted adhesion to surfaces or internal structures prior to use of an applicator device. For example, the adhesive material may only be releasable upon breaking or other opening of the pod. The non-adhesive material also may prevent unwanted adhesion prior to another activation or triggering event. For example, the non-adhesive material may be bio-resorbable, and upon absorption of the non-adhesive material, the pods may release the adhesive. The pod also may release the adhesive via other suitable arrangements.

In some embodiment the adhesive system is arranged to maintain a constant depth location where the adhesive is applied in relation to where the mesh joins the tissue. Such a constant depth location may be achieved by providing pods of a similar height, whether a thick or thin mesh prostheses is implanted in the body.

In some embodiments, the adhesive system is arranged to increase the likelihood of optimal surface contact between the adhesive and the mesh/tissue surfaces. For example, in some embodiments, the mesh may be marked with markings that indicate the locations of the pods. In such an example, the markings are located on the side of the mesh opposite to the side on which the pods are attached. As will be appreciated, such markings may assist a surgeon during application of the mesh. For example, the surgeon may use the markings to orient the mesh against the tissue structure, with the pods being positioned between the external side of the mesh and the tissue surface to which the mesh is attachable.

Figure 2:
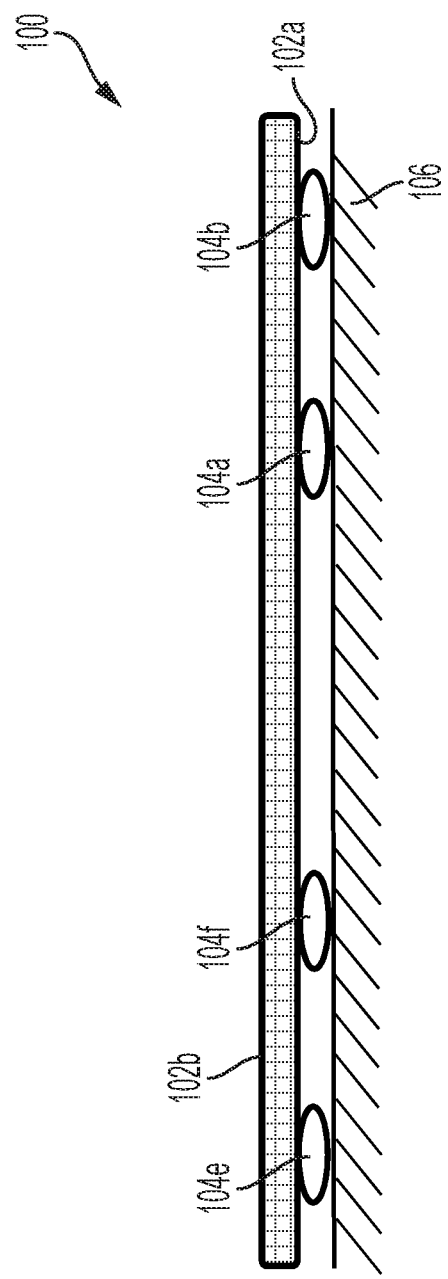
FIG. 2 is a cross-sectional schematic side view of the implantable prosthesis of FIG. 1A.

Turning now to the figures, FIG. 1A illustrates an example of a mesh prosthesis 100 with a pod adhesive system according to embodiments of the present disclosure. As shown in this figure, the prosthesis includes a prosthesis body configured to cover or plug a soft tissue defect. In some embodiments, the prosthesis includes multiple adhesive pods arranged to attach the prosthesis to the tissues structure. In some embodiments, the pods 104a-104f are located on a first side 102a of the prosthesis body. As shown in FIG. 2, the first side 102a of the prosthesis body is arranged to be facing and positioned adjacent to a tissue 106. In such embodiments, the pods 104a-104b project outwardly from the first side 102a of the prosthesis towards the tissue 106.

Although the prosthesis is shown as being generally oval, elliptical or egg shaped, it will be appreciated that the prosthesis may have different shapes in other embodiments. For example, in some embodiments, the prosthesis may be square or rectangular in shape. Also, although the prosthesis is shown as having six pods in these embodiments, the prosthesis may have any suitable number of pods. For example the prosthesis may include one, two, three, or more pods.

As will be appreciated, the pods may be positioned in any suitable arrangement and at any suitable location on the prosthesis as this aspect of the disclosure is not limited in this regard. For example, the pod(s) may be positioned at or near the periphery of the first side of the prosthesis. The pod(s) also may be positioned in a central region of the first side of the prosthesis. As shown in FIG. 1A, the pods may be arranged in a substantially oval arrangement. The pods also may be arranged in a square, rectangular, triangular, other polygonal or other suitably shaped arrangement.

Figure 1B:
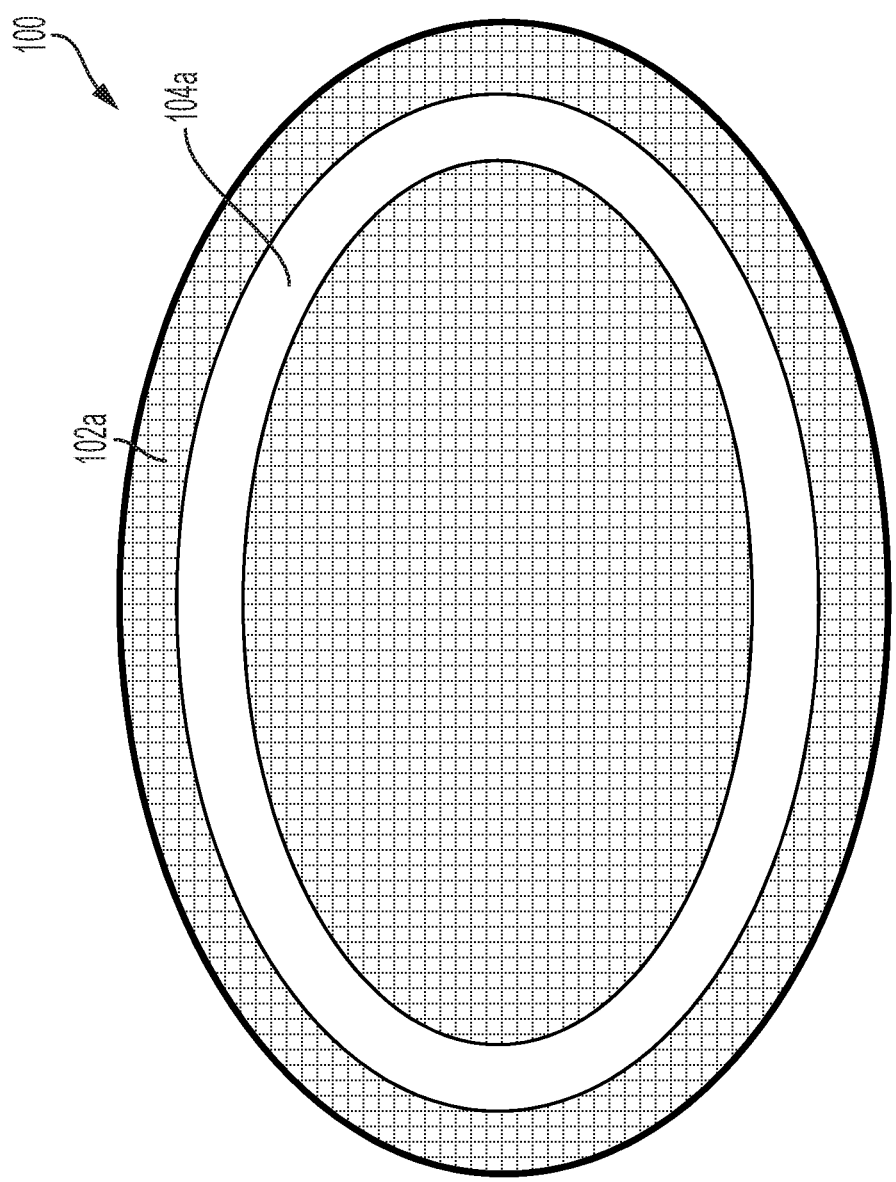
FIG. 1B is a schematic top view of an implantable prosthesis having a pod adhesive system according to other embodiments of the present disclosure.

Although the prosthesis in FIG. 1A is shown as having multiple pods arranged in a substantially oval arrangement near the periphery of the first side, in other embodiments, as shown in FIG. 1B, the prosthesis may include a single pod 104a extending around the periphery of the first side. In such an embodiment, the pod may be substantially annular or ring-shaped. The pod also may be formed of an elongated tube.

Figure 3A:
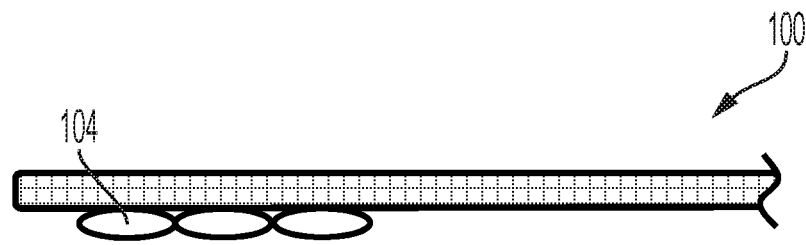
FIGS. 3A-3D are cross-sectional schematic side views of implantable prostheses according to several illustrative embodiments.
Figure 3B:
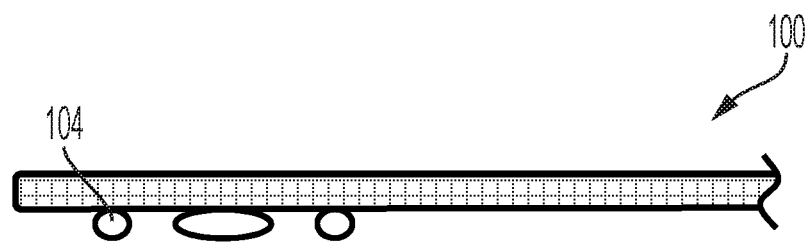
Figure 3C:
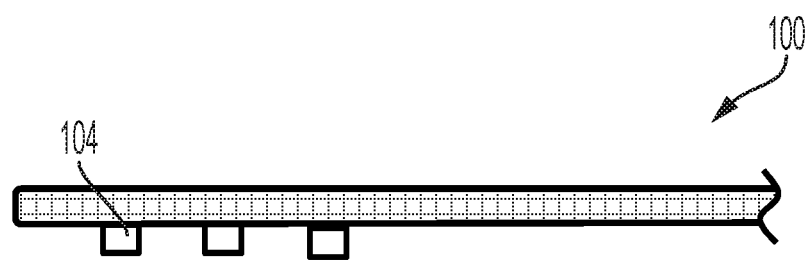
Figure 3D:
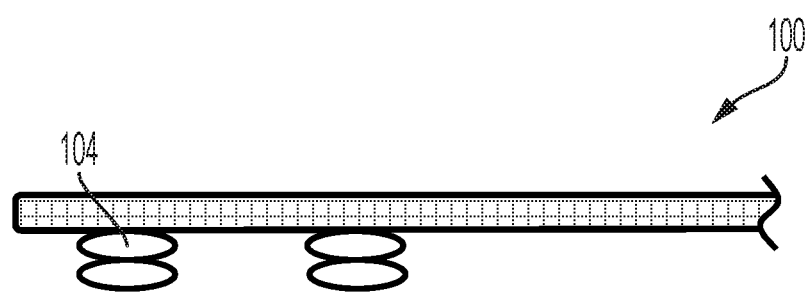

In some embodiments, as shown in FIGS. 1A and 2, the pods may be spaced apart from one another. In other embodiments, as shown in FIG. 3A, the pods may be adjacent to one another. In such embodiments, the adjacent pods may contact one another. For example, a first side of a first pod may be adjacent to and contact a second side of a second pod. In some embodiments, as shown in FIG. 3D, one more pods may be positioned on top of one another. For example, as shown in this figure, one or more pods may be vertically arranged in a column on the prosthesis. In one such example, the vertically arranged pods may have the same encapsulated adhesive. In another example, the vertically arranged pods may include a two-part adhesive, with a first pod having a base resin and a second having a hardener or activator.

In embodiments having more than one pod, the pods may be the same shape or may have different shapes. For example, as shown in FIGS. 1A, 2, 3A, and 3C-3D, the pods may all be same shape. In the embodiment illustrated in FIG. 3B, the pods may be different shapes. As will be appreciated, the pods may have any suitable shape. For example, the pods may be circular, square, triangular, rectangular, other polygonal or other suitable shape. The pods also may have any suitable cross-sectional shape. The pods may have any suitable height.

Figure 4:
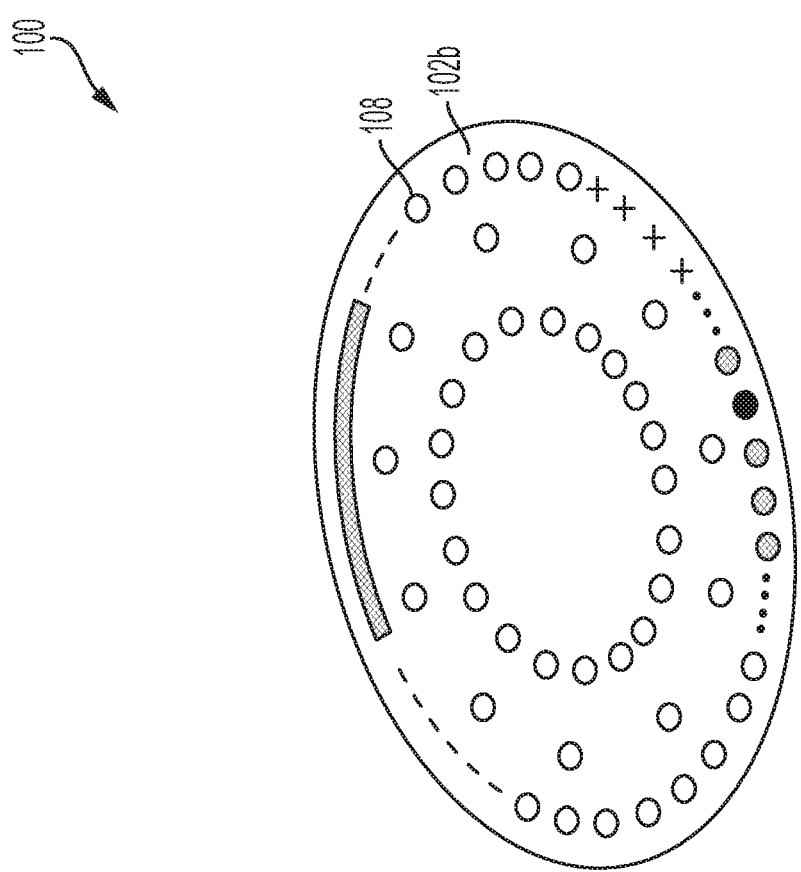
FIG. 4 illustrates pod markings on an internal side of an implantable prosthesis according to embodiments of the present disclosure.

FIG. 4 illustrates an example of markings 108 that may be included on a second side 102b of the mesh prosthesis. As will be appreciated, the markings may be any shape, size and color so as to indicate the general location of the pods on the first side 102a. The markings also may be used to indicate locations on the mesh where the pods are not located. The mesh also may include other markings to help the surgeon position or otherwise use the mesh.

FIGS. 5A-5D illustrate a method of attaching a mesh prosthesis to at least a portion of tissue structure having a defect. As shown in these figures, the mesh 100 has been oriented and placed against at least a portion of the tissue 106, with an adhesive pod 104 positioned in between the tissue and the mesh. In this position, the first side 102a of the mesh is facing the tissue and a second side 102b is facing away from the tissue (e.g., is internally facing). As will be appreciated, before placement, the mesh may be introduced into the body cavity and oriented via any suitable method. For example, the mesh may be inserted into the body cavity via a trocar cannula. In such an example a grasper or other surgical tool may be used to position the mesh relative to the defect.

As shown in these figures, a deployment device 110 may be placed against the second side 102b of the mesh. In some embodiments, the deployment device is placed at a target location on the second side of the mesh, such as at one of the markings on the second side of the mesh denoting the location of a first pod.

In some embodiments, the deployment device 110 includes a housing within which a piercer, needle 112, is disposed. As will be appreciated, other suitable piercers may be used in other embodiments. The needle may be connected to a shaft 114 or plunger that is arranged to drive movement of the needle back and forth. As will be appreciated, the surgeon may first insert the deployment device into the body cavity via a cannula. In some embodiments, the surgeon may drive movement of the shaft and needle by pressing a button on the deployment device. In other embodiments, the surgeon may direct a robotic arm to drive movement of the shaft and needle in the deployment device.

Figure 5A:
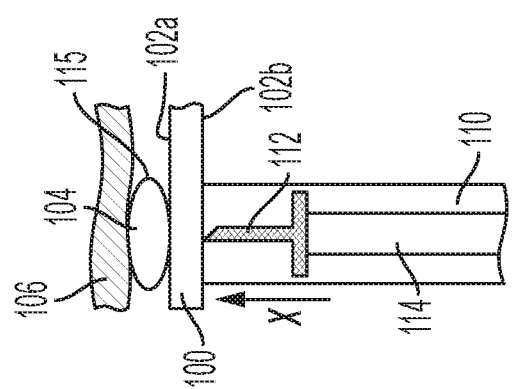
FIGS. 5A-5D illustrate a method of attaching an implantable prosthesis to tissue using a pod adhesive system according to one embodiment.
Figure 5B:
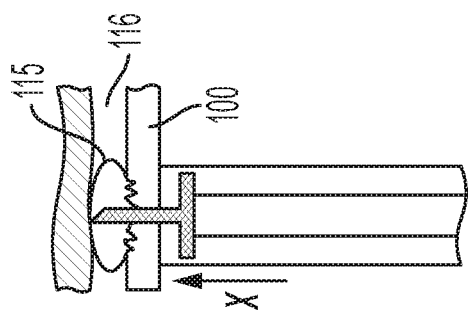

As shown in FIG. 5A, when actuated, the needle 112 and shaft 114 may be moved in a forward direction (see arrow X) towards the mesh and adhesive pod. As shown in FIG. 5B, the needle may be driven into the adhesive pod 104 and puncture the non-adhesive outer layer 115. Such puncturing may release the adhesive material into the space 116 between the mesh and the tissue. In some embodiments, in the puncturing position, the needle only punctures a first side of the adhesive pod, as is shown. The deployment device also may be arranged to puncture first and second sides of the adhesive pod (see FIG. 5C) when the needle is in the puncturing position. As will be appreciated, in the puncturing position, the needle may extend outwardly beyond a distal end of the deployment device. In some embodiments, a distal end of the needle may extend into the tissue in the puncturing position.

Figure 5C:
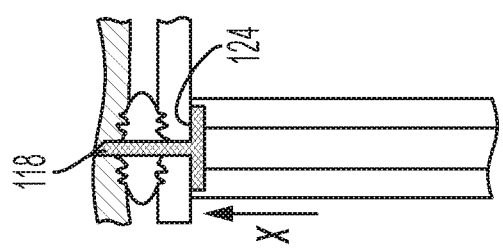
Figure 5D:
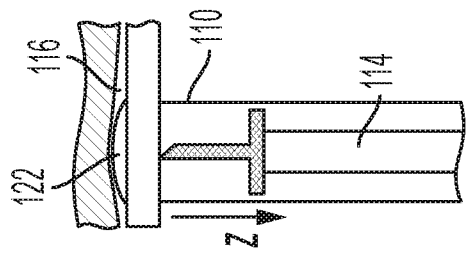

In some embodiments, as shown in FIG. 5C, the needle and shaft or plunger may be further moved in the forward direction (see arrow X in FIGS. 5B-5C) to compress the mesh against the tissue. In such embodiments, compression of the mesh and tissue may aid in distributing the adhesive behind the mesh and into a wider area of the space 116. An example of a distributed adhesive 122 is shown in FIG. 5D. In some embodiments, in the compression position, a distal end 118 of the needle may extend into the tissue.

In some embodiments, the compressive force is applied via a flat compression head 124 or surface formed on the needle. As shown in these figures, the flat compression head faces the second side of the mesh. In some embodiments, the needle is substantially T-shaped. In some embodiments, the flat compression head of the needle is located at a specified distance from a distal end of the needle. In some embodiments, the compression head advances to compress the mesh as the needle reaches the end of its stroke length. As will be appreciated, the deployment device may be arranged to compress the mesh with the compression head 124 for any desired period of time. As will be further appreciated, the compression surface may have other suitable shapes and arrangements.

In some embodiments, after puncturing the pod and compressing the mesh against the tissue, the shaft 114 may be moved in a direction away from the mesh and adhesive pod (see arrow Z in FIG. 5D) to retract the needle 112 back into the deployment device 110, leaving the mesh adhered to the tissue.

Once the needle has been retracted into the deployment device, the device may be moved to another location, e.g., to a second marking indicating the presence of a second pod, and the above steps may be repeated to release an adhesive from the second pod. These steps can be further repeated to release an adhesive from third, fourth, or more pods on the mesh.

Figure 6C:
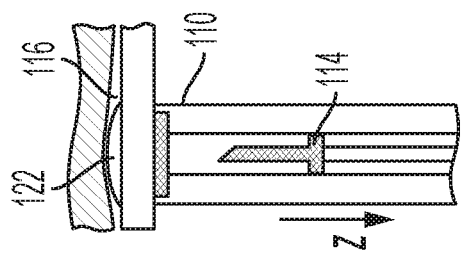
FIGS. 6A-6C illustrate a method of attaching an implantable prosthesis to tissue using a pod adhesive system according to another embodiment.
Figure 6B:
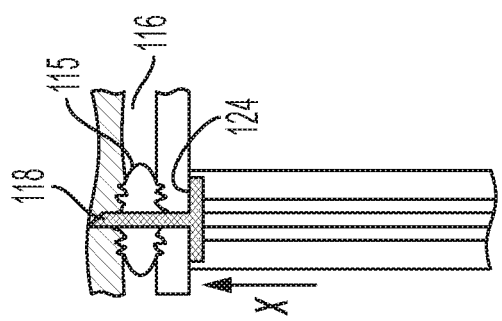
Figure 6A:
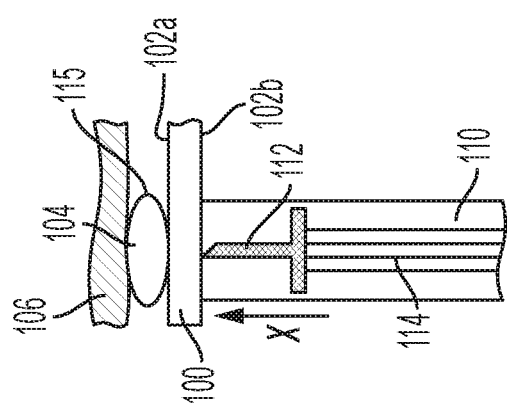

Although the needle and compression head are shown as being retracted together in FIG. 5D, in other embodiments, as show in FIGS. 6A-6C, the needle 112 may be moved forward with the compression head 124 but may be retracted independent of the compression head. As will be appreciated, in such an example, the piercer may include a two-part piercer with a needle portion and a compression head portion. In some embodiments, the needle may be retracted after the needle reaches the end of its stroke length. In such embodiments, the needle may be retracted while the compression head remains in the forward position for a longer period of time to compress the mesh and tissue (see FIG. 6C). In some embodiments, the needle may be retracted into the shaft or plunger attached to the compression head.

As will be appreciated, all of the pods on the mesh need not be punctured during a surgical procedure. For example, one or more pods may be punctured during the surgical procedure to release the adhesive while one or more pods may remain intact during the surgical procedure but may release adhesive during the initial healing process (e.g., by having the outer layer be resorbed, as described).

Although the method in FIGS. 5A-5D shows the mesh being compressed against the tissue to distribute the adhesive, in some embodiments, the mesh is not compressed after the pod is punctured. For example, after puncturing the pod to release the adhesive, the needle may be simply retracted back into the deployment device.

Although the deployment device 110 used in the method illustrated in FIGS. 5A-5D includes a single needle connected to the shaft for puncturing a single pod, in other embodiments, the needle may be arranged to puncture more than one pod. For example, in embodiments in which the prosthesis has more than one stacked pod (see FIG. 3D), the needle may be arranged to puncture both pods when the needle and shaft are moved in the forward direction (see arrow X). As will be appreciated, in such embodiments, the needle may be longer than that shown in FIGS. 5A-5D.

Figure 7C:
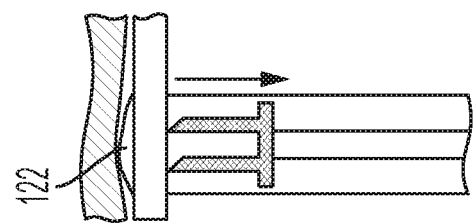
FIGS. 7A-7C illustrate a method of attaching an implantable prosthesis to tissue using a pod adhesive system according to still another embodiment.
Figure 7B:
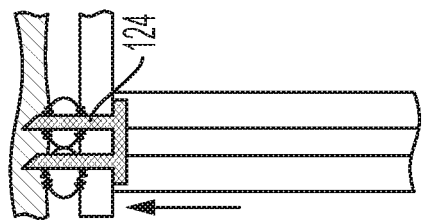
Figure 7A:
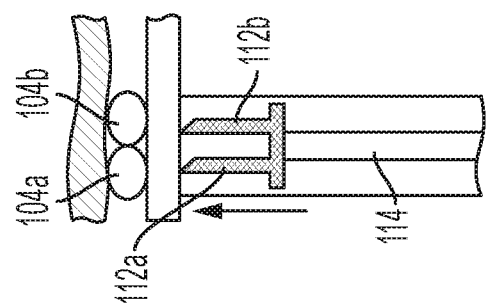

In other embodiments, as shown in FIGS. 7A-7C, the deployment device may include more than one needle connected to the shaft. For example, as shown in these figures, first and second needles 112a, 112b may be connected to the shaft 114 for puncturing first and second pods 104a, 104b, respectively. As with other embodiments, the first and second needles may have a flat compression head 124 or surface for compressing the mesh against the tissue.

Although the first and second needles are connected to the same compression head and shaft in this embodiment, in other embodiments, each needle may be connected to its own shaft and have a respective compression head.

As will be appreciated, although the deployment device is shown has having one and two needles in these embodiments, the deployment device may have more than two needles in other embodiments. In such embodiments, the needles may be arranged in any suitable arrangement (e.g., linearly, in a circle, etc.) in the deployment device.

Figure 8:
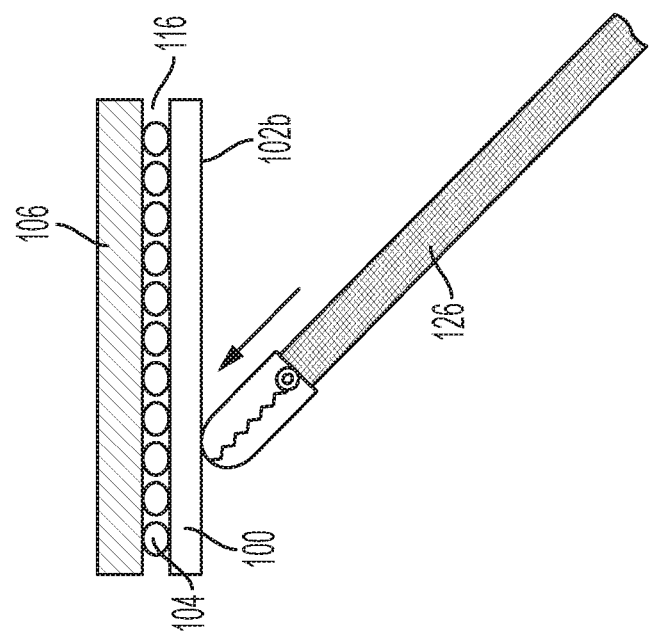
FIG. 8 illustrates a method of attaching an implantable prosthesis to tissue using a pod adhesive system according to still another embodiment.

Although the adhesive pods are shown as being punctured to release the adhesive between the mesh and the tissue, the adhesive may be released from the pods in other suitable manners. In some embodiments, as show in FIG. 8, the pods may be rupturable via pressure applied to the mesh via a surgical instrument 126. For example, a surgeon may apply light pressure to a second side 102b of the mesh with blunt graspers. As with other embodiments, upon rupturing of the pods, the adhesive may be released into the space 116 between the mesh and the tissue. In some embodiments, the pressure applied to the mesh via the surgical instrument also may apply a compressive force to distribute the adhesive in the space between the mesh and the tissue.

According to another aspect, a method of repairing a soft tissue defect of a tissue structure with an implantable prosthesis is disclosed. In some embodiments, the method includes placing the mesh prosthesis relative to a tissue defect to be repaired. In some embodiments, placing the mesh prosthesis includes using placing the prosthesis against the tissue such that one or more adhesive-filled pods are located in between the tissue and the mesh. In some embodiments, placing the mesh includes using one or more markings on a second side of the mesh to orient the mesh relative to the defect. In some embodiments, the method includes releasing an adhesive into the space between the mesh and the tissue. For example, the pods may be punctured and/or ruptured, as described, to release the adhesive. The method may also include applying a compressive force to distribute the adhesive in this space. In some embodiments, the method includes releasing the adhesive in a second pod into the space between the mesh and tissue.

The pods may be formed via any suitable method as the disclosure is not limited in this regard. For example, the pods may be formed by heat sealing an adhesive in PVC shrink wrap sheets. In such an example, the shrink wrap sheets form the non-adhesive outer layer of the pod As will be appreciated, the thickness of the outer layer and/or the size of the pod may vary depending upon the method of releasing the adhesive. For example, in embodiments in which the pods are to be punctured by the needle, the pods may be larger and/or have a thicker outer layer. In embodiments in which the pods are to be ruptured by lighter pressure applied by a surgical instrument, the pods may be smaller and/or have a thinner outer layer.

The pods may be attached to the mesh via any suitable method as this aspect of the disclosure is also not limited in this regards. For example, the pods may be glued to the mesh in some embodiments. In other embodiments, the pods may be sewn onto or into the mesh.

In some embodiments, the prosthetic repair fabric may include a polypropylene mesh which may promote rapid tissue or muscle ingrowth into and around the mesh structure. Other surgical materials which are suitable for tissue or muscle reinforcement and defect correction also may be utilized, including BARD MESH (available from C.R. Bard, Inc.), SOFT TISSUE PATCH, SURGIPRO, TRELEX, PROLENE and MERSILENE, and other mesh materials. Resorbable materials, including polyglactin (VICRYL) and polyglycolic acid (DEXON), may be suitable for applications involving temporary correction of tissue or muscle defects. Collagen materials such as COOK SURGISIS also may be used.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An implantable prosthesis for repairing a soft tissue defect, the implantable prosthesis comprising:
   a prosthesis body having a first side arranged to face a tissue structure having a defect and second side opposite the first side;
   one or more adhesive-filled pods disposed on the first side of the body, the one or more adhesive filled pods being selectively openable to supply an adhesive, wherein the one or more pods include individual first and second pods having outer surfaces, wherein the outer surface of the first pod is positioned in contact with the outer surface of the second pod.

2. The implantable prosthesis of claim 1, wherein the one or more pods include first and second pods, wherein the first pod is filled with a base resin and the second pod is filled with a least one of an actuator and a hardener.

3. The implantable prosthesis of claim 1, wherein the one or more pods are positioned at or near a periphery of the prosthesis body.

4. The implantable prosthesis of claim 1, wherein the one or more pods are positioned in a central region of the first side of the prosthesis body.

5. The implantable prosthesis of claim 1, wherein the first pod is stacked on top of the second pod relative to the first side of the body.

6. The implantable prosthesis of claim 1, wherein the first and second pods are the same size.

7. The implantable prosthesis of claim 1, wherein the first and second pods are different sizes.

8. The implantable prosthesis of claim 1, wherein the one or more pods are selected from a group consisting of pierceable, breakable, puncturable and burstable pods.

9. The implantable prosthesis of claim 1, wherein the one or more pods includes an adhesive material encapsulated in a non-adhesive material.

10. The implantable prosthesis of claim 9, wherein the non-adhesive material includes a bio-resorbable material.

11. The implantable prosthesis of claim 1, in combination with a deployment device arranged to selectively open the one or more pods.

12. The combination of claim 11, wherein the deployment device includes a surgical instrument.

13. The combination of claim 11, wherein the deployment device includes a piercer arranged to pierce the one or more pods.

* * * * *

UNITED STATES PATENT AND TRADEMARK OFFICE
CERTIFICATE OF CORRECTION

PATENT NO. : 12,109,101 B2  
APPLICATION NO. : 16/976659  
DATED : October 8, 2024  
INVENTOR(S) : Jonathan Bruce Trexler Page 1 of 1

It is certified that error appears in the above-identified patent and that said Letters Patent is hereby corrected as shown below:

In the Claims

At Column 8, Claim 2, Lines 27-28: "The implantable prosthesis of claim 1, wherein the one or more pods include first and second pods, wherein the first pod" should read --The implantable prosthesis of claim 1, wherein the first pod--

Signed and Sealed this  
Twenty-sixth Day of November, 2024

Katherine Kelly Vidal  
*Director of the United States Patent and Trademark Office*